(12) United States Patent
Stamler et al.

(10) Patent No.: US 11,518,748 B2
(45) Date of Patent: Dec. 6, 2022

(54) ALDOKETO REDUCTASE INHIBITORS AND USES THEREOF

(71) Applicant: case western reserve university, Cleveland, OH (US)

(72) Inventors: Jonathan S. Stamler, Shaker Heights, OH (US); William Greenlee, Cleveland, OH (US); Focco van den Akker, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 17/278,559

(22) PCT Filed: Sep. 23, 2019

(86) PCT No.: PCT/US2019/052426
§ 371 (c)(1),
(2) Date: Mar. 22, 2021

(87) PCT Pub. No.: WO2020/061566
PCT Pub. Date: Mar. 26, 2020

(65) Prior Publication Data
US 2021/0347744 A1 Nov. 11, 2021

Related U.S. Application Data

(60) Provisional application No. 62/734,560, filed on Sep. 21, 2018.

(51) Int. Cl.
| C07D 263/52 | (2006.01) |
| C07D 209/96 | (2006.01) |
| C07D 235/02 | (2006.01) |

(52) U.S. Cl.
CPC ......... *C07D 263/52* (2013.01); *C07D 209/96* (2013.01); *C07D 235/02* (2013.01)

(58) Field of Classification Search
CPC .......................... C07D 235/02; A61K 31/4184
See application file for complete search history.

(56) References Cited

U.S. PATENT DOCUMENTS

| 2,683,718 | A  | 7/1954  | Dornfeld et al. |
| 4,436,745 | A  | 3/1984  | York, Jr. |
| 5,153,211 | A  | 10/1992 | York, Jr. |
| 7,674,795 | B2 | 3/2010  | Mailliet et al. |
| 10,117,842 | B2 | 11/2018 | Nagy |
| 10,537,557 | B2 | 1/2020  | Raffay et al. |
| 2010/0292178 | A1 | 11/2010 | Young |
| 2010/0305078 | A1 | 12/2010 | Schotzinger et al. |
| 2011/0092566 | A1 | 4/2011  | Srivastava et al. |
| 2012/0083501 | A1 | 4/2012  | Hunt et al. |
| 2012/0220001 | A1 | 8/2012  | Philippe |
| 2013/0196342 | A1 | 8/2013  | Stamler et al. |
| 2014/0206693 | A1 | 7/2014  | Srivastava et al. |
| 2017/0360755 | A1 | 12/2017 | Stamler |

FOREIGN PATENT DOCUMENTS

| EP | 1961420 A1 | 8/2008 |
| EP | 1987829 A1 | 11/2008 |
| WO | 2002/047680 A2 | 6/2002 |
| WO | 2004/110488 A1 | 12/2004 |
| WO | 2008/118370 A2 | 10/2008 |
| WO | 2010/104595 A1 | 9/2010 |
| WO | 2016090373 A1 | 6/2016 |

OTHER PUBLICATIONS

Jonathan S. Stamler; "Compositions and Methods of Reducing Serum Cholesterol and PCSK9"; U.S. Appl. No. 16/648,737, filed Mar. 19, 2020; U.S. Non-Final Office Action dated Mar. 7, 2022; 19 pgs.
PubChem-CID-10335836, Create Date: Oct. 25, 2006; p. 2.
Applicant: Case Western Reserve University; PCT International Application No. PCT/US19/52426, Filed: Sep. 23, 2019; PCT International Search Report and Written Opinion, Authorized Officer: Lee Young; Feb. 7, 2020; 9 pgs.
Barski et al. "Tho Aldo-Keto Reductase Superfamily and its Rult:, in Drug Metabolism and Detoxification" Drug Metabolism Reviews. Nov. 6, 2008 (Nov. 6, 2008), vol. 40, p. 553-624.
Fletcher, "What should my cholesterol level be at my age?" Medical News Today. Feb. 20, 2017 (Feb. 20, 2017) https://www.medicalnewstoday.com/articles/315900.php; p. 2, para 2.
Hwang et al. The FASEB Journal, Published online Dec. 2001, pp. 1-22.
International Search Report & Written Opinion for International Application No. PCT/US2015/064308.
Malatkova, Pet al., "Human Carbonyl Reductases", Current Drug Metabolism, vol. 11, 2010, 24 pp. 639-658.
Morakinyo, MK et al., "Detailed mechanistic investigation into the Snitrosation of cysteamine", 26 Can J. Chem. vol. 90, 2012, pp. 724-738.
Morris, SL et al., "Inhibition of Bacillus cereus Spore Outgrowth by Covalent Modification of a Sulfhydryl Group by Nitrosothiol and Iodoacetate", Journal of Bacteriology, vol. 148, No. 2, Nov. 1981, pp. 465-471.
Partial Supplementary European Search Report for Application No. 15864966.5-1112/3226859.
PubChem CID 20267156, create date, Dec. 5, 2007 p. 2 formula.
PubChem CID 20267160, create date, Dec. 5, 2007 p. 1 formula.
Puneet Anand et al., "Identification of S-nitroso-CoA reductases that regulate protein S-nitrosylation", Proceedings of the National Academy of Sciences, vol. 111, No. 52, Dec. 15, 2014, pp. 8572-18577.
Puneet Anand, "Purification and Characterization of Novel Denitrosylases from Yeast and Mammals", Dec. 31, 2012, pp. 1-156.
Roediger, Wew. Review article: nitric oxide from dysbiotic bacterial respiration of nitrate in the pathogenesis and as a target for therapy of ulcerative colitis "Ailment Pharmacol", Ther. vol. 27, 2008, pp. 531-541.

(Continued)

*Primary Examiner* — Kamal A Saeed
(74) *Attorney, Agent, or Firm* — Tarolli, Sundheim, Covell & Tummino LLP

(57) ABSTRACT

Aldoketo reductase (AKR) inhibitors having formulas I-III are used to treat disorders associated with NO/SNO deficiency.

16 Claims, 4 Drawing Sheets

(56) References Cited

OTHER PUBLICATIONS

Soda, M et al., "Inhibition of Human Aldose Reductase-Like Protein (AKR1810) by alpha- and gamma-Mangostins, Major Components of Pericarps of Mangosteen", Biol Pharm. Bull. vol. 35, No. 11, 2012, pp. 2075-2080.
Supplemental European search report for application No. 15864966.5-1112/3226859, dated Nov. 30, 2018.
Suropean Search Report for application No. 15864966.5-1112/3226859.
Tao B et al: "Synthesis of Conformationally Constrained Spirohydantoins With a Dibenzoaa, Doheptadiene Ring", Synthesis, Georg Thieme Verlag, Stutigart, DE, No. 10, Feb. 29, 2000, pp. 1449-1453.
Zhang, HH et al., "Estrogen-Responsive nitroso-Proteorne in Uterine Artery Endothelial Cells: Role of Endothelial Nitric Oxide Synthase and Estrogen Receptor-beta", J. Cell Physiol. vol. 227, No. 1, Jan. 2012, pp. 146-159.

ALDOKETO REDUCTASE INHIBITORS AND USES THEREOF

RELATED APPLICATION

This application claims priority from U.S. Provisional Application No. 62/734,560, filed Sep. 21, 2018, the subject matter of which is incorporated herein by reference in its entirety.

TECHNICAL FIELD

This application relates compounds that can be used as aldoketo reductase (AKR) inhibitors, and particularly relates to the use of the compounds as AKR inhibitors to treat disorders associated with NO/SNO deficiency.

BACKGROUND

The chemical compound nitric oxide is a gas with the chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO capable of controlling biological events between adjacent cells and within cells, but present problems with the ability to regulate its activity.

As free radical gas, NO is reactive and unstable, thus NO is short lived in vivo, having a half life of 3-5 seconds or less under physiologic conditions. In the presence of oxygen or metals, NO can combine with thiols to generate a biologically important class of stable NO adducts called S-nitrosothiols (SNO's). This stable pool of NO has been postulated to act as a regulated source of bioactive NO and as such appears to be important in health and disease, given the centrality of NO in cellular homeostasis (Stamler et al., Proc. Natl. Acad. Sci. USA, 89:7674-7677 (1992)). Protein SNO's play broad roles in the function of cardiovascular, respiratory, metabolic, gastrointestinal, immune, and central nervous system (Foster et al., Trends in Molecular Medicine, 9 (4):160-168, (2003)). Low molecular weight SNOs provide NO bioactivity that is specific to the nature of the molecule. Heretofore the biology of low molecular weight SNOs was identified with S-nitrosoglutathione (GSNO).

Currently, there is a great need in the art for diagnostics, prophylaxis, ameliorations, and treatments for medical conditions relating to increased NO synthesis and/or increased NO bioactivity. There is need for regulating individual SNOs. In addition, there is a significant need for novel compounds, compositions, and methods for preventing, ameliorating, or reversing other SNO-associated disorders. The only available means to raise GSNO is through inhibition of known GSNO reductases, primarily ADH3 (glutathione dependent formaldehyde dehydrogenase) and carbonyl reductase.

SUMMARY

Embodiments described herein relate to compounds that can be used as aldoketo reductase (AKR) inhibitors and to their use in modulating protein nitrosylation and treating disorders associated with NO/SNO deficiency. The compounds described herein can have a formula selected from the group consisting of:

(I)

(II)

and pharmaceutically acceptable salts thereof;

wherein $X^1$ and $X^3$ are each independently $CH_2$, NH, or O;

$X^2$ and $X^4$ are each independently a linear or branched alkylene, alkylyne, O, or absent;

$R^1$ and $R^4$ are each independently a substituted or unsubstituted cycloalkyl or a substituted or unsubstituted heterocyclyl containing from 4-6 ring atoms (wherein 1 atom of the ring atoms is independently selected from O);

$R^2$, $R^3$, $R^5$, and $R^6$ are each independently H, a halo group, $C_1$-$C_6$ alkyl, $C_1$-$C_6$ alkoxy, alkylsulfide, $C_1$-$C_6$ alkylsulfinyl, alkylsulfonyl, $-CF_3$, $-S-CF_3$, $-SO_2CF_3$, $CO-N(R^a)-R^b$, $C_1$-$C_6$ alkyl alcohol, $C_1$-$C_6$ alkyl ether, nitro, $C_1$-$C_6$ alkyl sulfide, $C_1$-$C_6$ alkylamine, $C_1$-$C_6$ alkyl esters, carboxylic acids, $C_1$-$C_6$ cycloalkyl, or $C_1$-$C_6$ heterocyclyl; and $R^a$ and $R^b$ are each independently H or a $C_1$-$C_6$ alkyl.

In some embodiments, the 7-C of the compound of formula (I) does not include an $R^2$ group selected from the group consisting of hydrogen, cyclopropyl, fluoro if the 2-C is a cyclopropyl or cyclobutyl group, $X^1$ is NH, and $X^2$ is absent.

In other embodiments, $R^1$ and $R^4$ are each independently a substituted or unsubstituted cyclopropyl, cyclobutyl, bicyclobutyl, or oxacyclobutyl.

In some embodiments, $X^1$ and $X^3$ are NH.

In other embodiments, $X^2$ and $X^4$ are absent.

In other embodiments, $R^2$, $R^3$, $R^5$, and $R^6$ are each independently H, a halo group, or a $C_1$-$C_6$ alkyl.

In still other embodiments, the compound can have the following formula (III):

(III)

or pharmaceutically acceptable salts thereof;

wherein $X^1$ is $CH_2$, NH, or O;

$R^2$ and $R^3$ are each independently H, a halo group, $C_1$-$C_6$ alkyl, $C_1$-$C_6$ alkoxy, $C_1$-$C_6$ alkylsulfide, $C_1$-$C_6$ alkylsulfinyl, $C_1$-$C_6$ alkylsulfonyl, —$CF_3$, —S—$CF_3$, —$SO_2CF_3$, CO—N($R^a$)—$R^b$, $C_1$-$C_6$ alkyl alcohol, $C_1$-$C_6$ alkyl ether, nitro, $C_1$-$C_6$ alkyl sulfide, $C_1$-$C_6$ alkylamine, $C_1$-$C_6$ alkyl esters, carboxylic acids, $C_1$-$C_6$ cycloalkyl, or $C_1$-$C_6$ heterocyclyl;

$R^a$ and $R^b$ are each independently H or a $C_1$-$C_6$ alkyl; and $R^7$ and $R^8$ are each independently H, a halo group, or $C_1$-$C_6$ alkyl.

In some embodiments, the 7-C of the compound does not include an $R^2$ group selected from the group consisting of hydrogen, cyclopropyl, and fluoro.

In some embodiments, the compound can have a formula selected from the group consisting of:

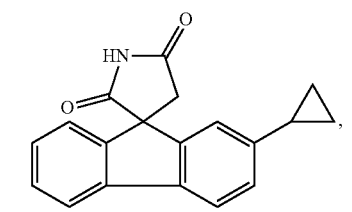

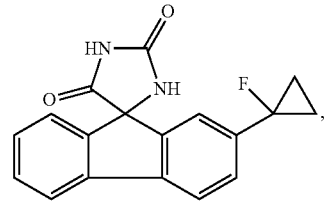

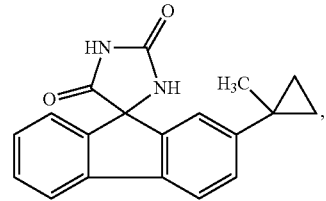

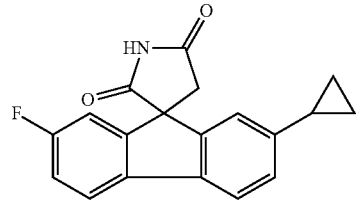

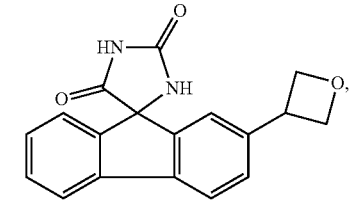

-continued

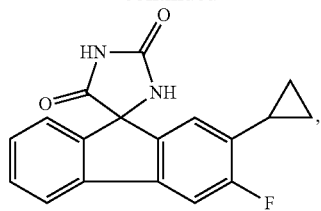

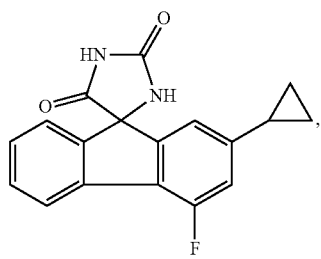

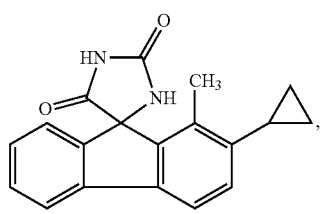

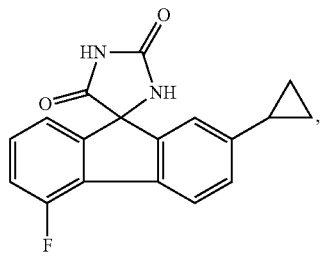

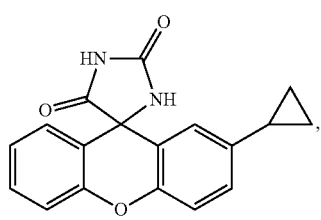

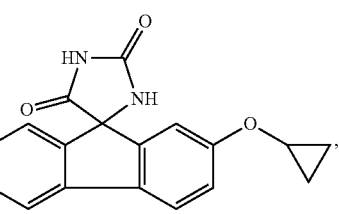

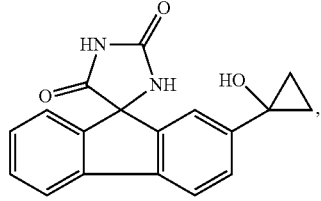

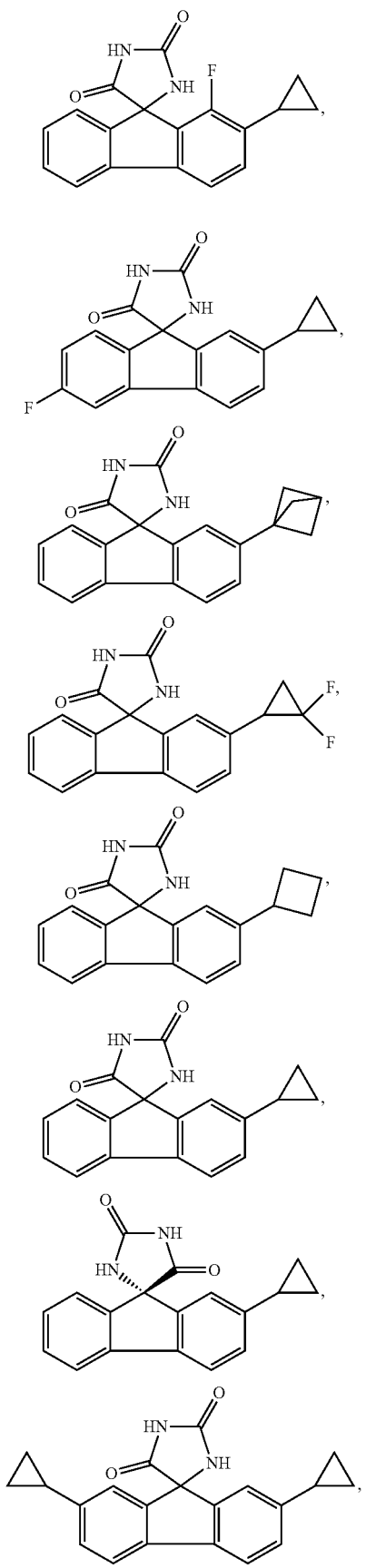
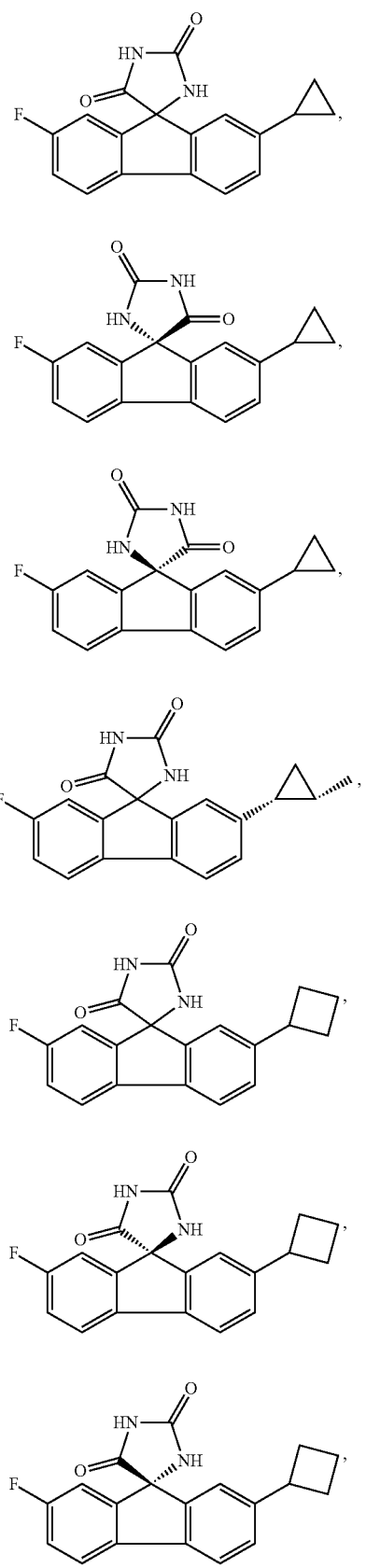
and pharmaceutically acceptable salts thereof.

In other embodiments, the compound can have a formula selected from the group consisting of:
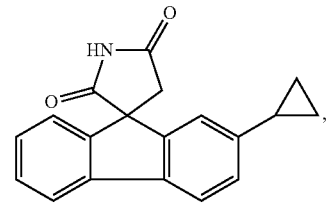,
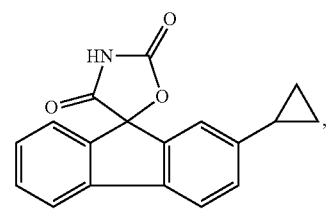,
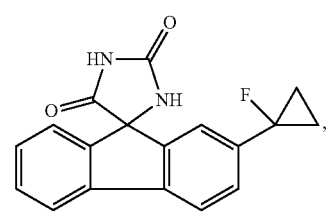,
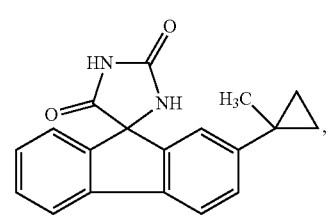,
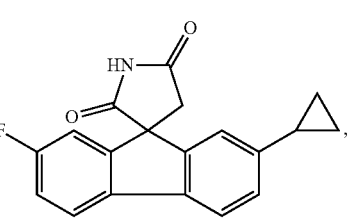,
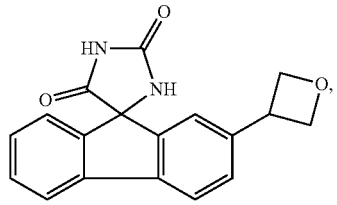,
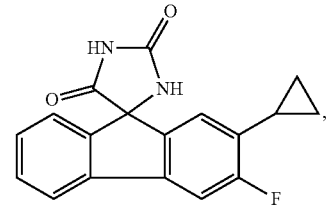,
-continued
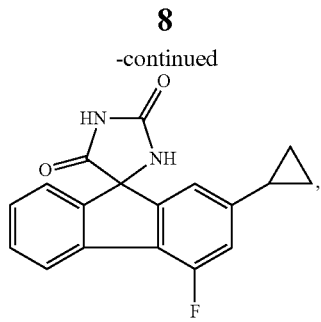,
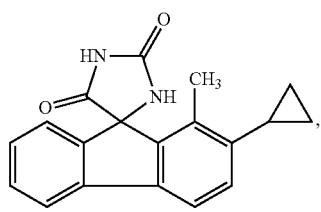,
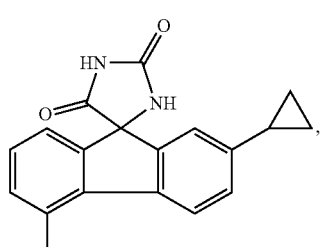,
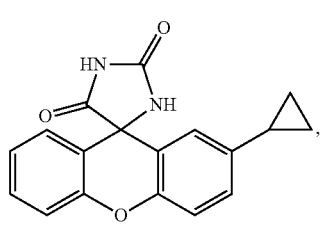,
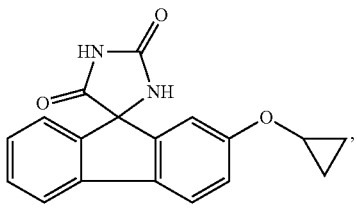,
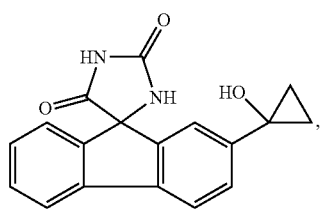,
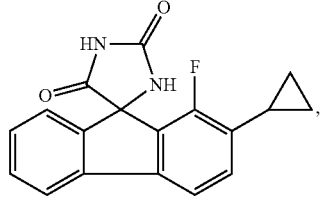, -continued

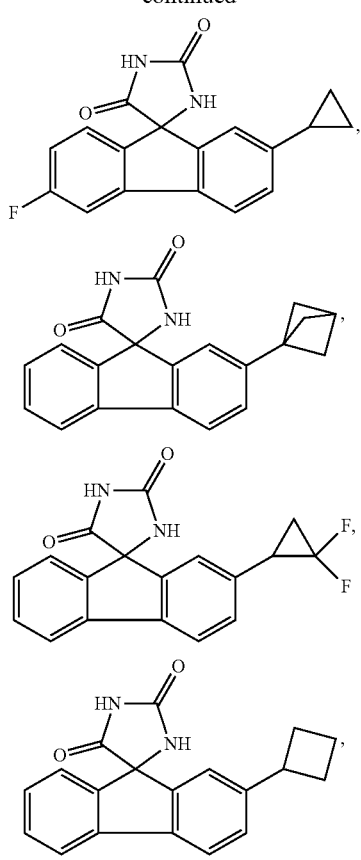

and pharmaceutically acceptable salts thereof.

In some embodiments, the compound can have the formula (IV):

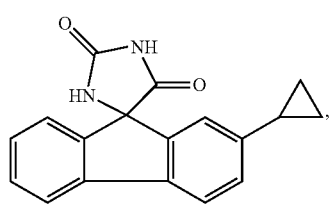
(IV)

and pharmaceutically acceptable salts thereof.

In other embodiments, the compound can have the following formula (IVa):

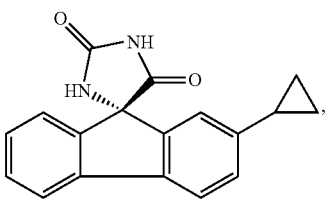
(IVa)

and pharmaceutically acceptable salts thereof.

In other embodiments, the compound can have the following formula (IVb):

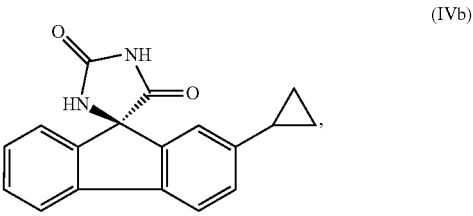
(IVb)

and pharmaceutically acceptable salts thereof.

In other embodiments, the compound can comprise an optical isomer of a compound having formula (IV). In some embodiments, the compound can comprise a mixture of at least one of an IVa or IVb optical isomer of a compound having formula (IV). For example, the compound can comprise a mixture of: less than about 50% by weight of the (IVa) optical isomer and greater than about 50% by weight of (IVb) optical isomer of a compound having formula (IV), less than about 25% by weight of the (IVa) optical isomer of a compound having formula (IV) and greater than about 75% by weight of the (IVb) optical isomer of a compound having formula (IV), less than about 10% by weight of the (IVa) optical isomer of a compound having formula (IV) and greater than about 90% by weight of the (IVb) optical isomer of a compound having formula (IV), less than about 1% by weight of the (IVa) optical isomer of a compound having formula (IV) and greater than about 99% by weight of the (IVb) optical isomer of a compound having formula (IV), greater than about 50% by weight of the (IVa) optical isomer of a compound having formula (IV) and less than about 50% by weight of the (IVb) optical isomer of a compound having formula (IV), greater than about 75% by weight of the (IVa) optical isomer of a compound having formula (IV) and less than about 25% by weight of the (IVb) optical isomer of a compound having formula (IV), greater than about 90% by weight of the (IVa) optical isomer of a compound having formula (IV) and less than about 10% by weight of the (IVb) optical isomer of a compound having formula (IV), or greater than about 99% by weight of the (IVa) optical isomer of a compound having formula (IV) and less than about 1% by weight of the (IVb) optical isomer of a compound having formula (IV).

In a still further embodiment, the compound can consist essentially of or consist of the (IVa) optical isomer of a compound having formula (IV). In yet another embodiment, the compound can consist essentially of or consist of the (IVb) optical isomer of a compound having formula (IV).

In other embodiments, the compound does not have a having a formula selected from the group consisting of:

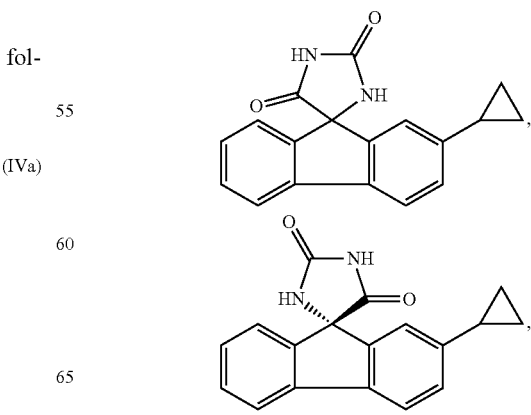

-continued

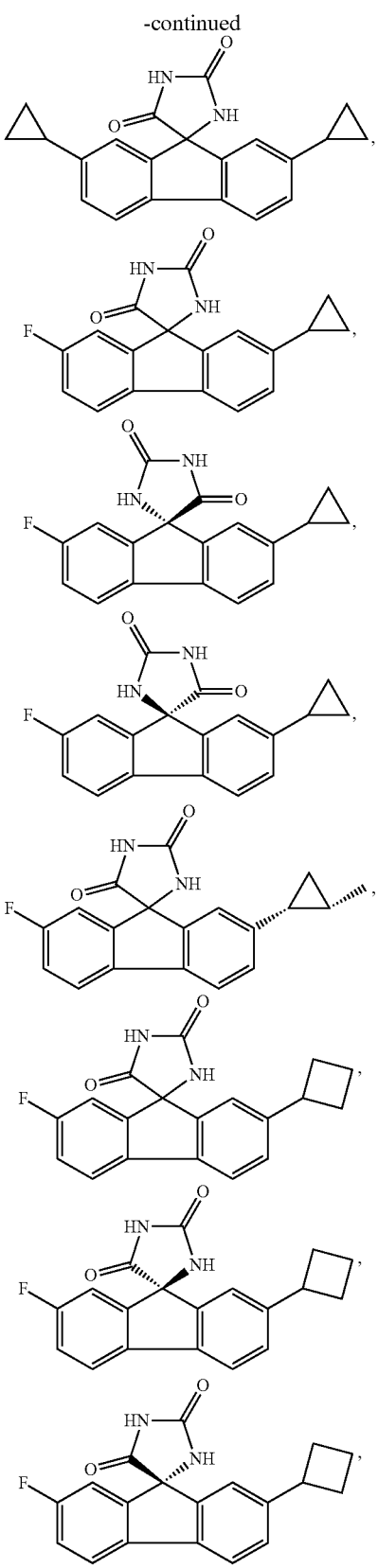

and pharmaceutically acceptable salts thereof.

In other embodiments, the compound is a selective or partially selective AKR1A1 inhibitor. For example, the compound can have a AKR1A1 to AKR1B1 selectivity (AKR1A1/AKR1B1) of at least about 1, at least about 2, at least about 3, at least about 4, at least about 5, or more.

AKR1A1 was found to reduce SNO-Coenzyme A (SNO-CoA), an endogenous nitrosylating agent, and thus is responsible for denitrosylation of multiple novel proteins. AKR1A1 was also found to metabolize GSNO, a known nitrosylating agent. Inhibition of AKRs (e.g., AKR1A1) can raise SNO levels and increase the S-nitrosylation of unique sets of proteins, which regulate cell metabolism. Administration of AKR inhibitors described herein to a subject can raise SNO levels in the subject, promote protein S-nitrosylation, and treat disorders associated with NO/SNO deficiency.

Multiple diseases and pathological conditions are associated with disruptions in protein S-nitrosylation. For example, it has been shown that storage of red blood cells (RBCs) leads to a rapid depletion of S-nitrosylated hemoglobin (SNO-Hb), a principal regulator of tissue oxygen delivery. In addition, heart disease, diabetes, cystic fibrosis, asthma, sickle cell disease, pulmonary hypertension, stroke, multiple sclerosis, and ischemia are among the many conditions characterized by diminished SNOs. Loss of SNO-Hb also impairs the ability of banked blood to dilate blood vessels after transfusion, resulting in exacerbation rather than correction of anemia-induced reduction in tissue oxygenation. SNO CoA-metabolizing enzymes are identified as regulators of cholesterol metabolism and sterol biosynthesis. Additionally, SNO-CoA metabolizing enzymes have regenerative capacity and protective function through metabolic reprogramming and may be useful in acute injury such as myocardial infarction, acute kidney injury, cardiac arrest, stroke, acute lung injury, liver injury, and traumatic brain injury, and in degenerative diseases such as heart failure, Alzheimer's disease, Huntington's, ALS, and Parkinson's disease.

Accordingly, in some embodiments AKR inhibitors described herein can be administered to a subject to raise SNO levels and increase S-nitrosylation of proteins in the subject and treat disorders associated with NO/SNO deficiency or disruptions in protein S-nitrosylation, promote maintenance (or restoration) of SNO-Hb levels ("renitrosylation"), lower cholesterol levels, treat ischemia, and treat disorders associated with NO/SNO deficiency, such as cystic fibrosis, asthma, inflammatory bowel disease, hypertension, heart failure, acute coronary syndromes, impotence, stroke, septic shock, as well as promote liver regeneration, stem cell enhancement, antimicrobial activity, and protect against ischemic injury, including renal ischemia and cardiac ischemia.

Other embodiments described herein relate to methods of treating a disorder ameliorated by NO donor therapy in a subject in need thereof. Such a method comprises administering a therapeutically effective amount of a pharmaceutical composition comprising at an AKR inhibitor described herein or a pharmaceutically acceptable salt, stereoisomer, prodrug, or metabolite thereof, in combination with at least one pharmaceutically acceptable carrier.

DETAILED DESCRIPTION

Figure 1:
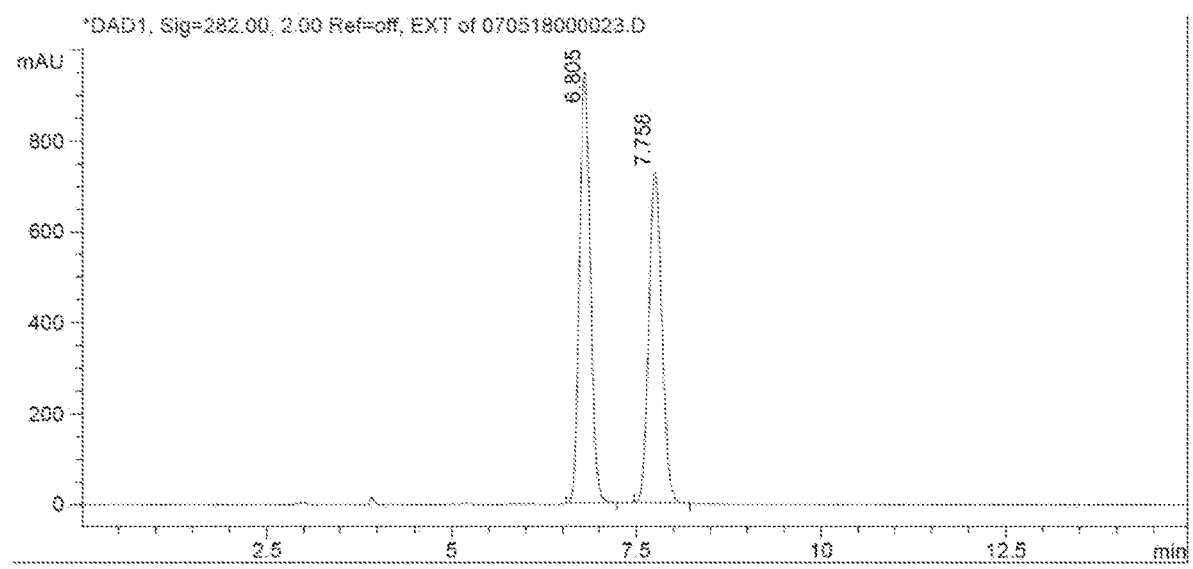
FIGS. 1-4 illustrate chromatograph and nmr spectra showing separation and characterization of the enantiomers of JSD-26-1.

For convenience, certain terms employed in the specification, examples, and appended claims are collected here.

Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl, and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The term sulfoxide refers to a sulfur attached to 2 different carbon atoms and one oxygen and the S—O bond can be graphically represented with a double bond (S═O), a single bond without charges (S—O) or a single bond with charges [S(+)—O(−)].

The terms "substituted" as in "substituted alkyl," and the like is meant that in the alkyl or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—ON$^+$C$^-$), isothiocyanato (—S—CN), azido (—N═N$^+$═N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR═NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—NO$_2$), nitroso (—NO), sulfo (—SO$_2$—OH), sulfonato (—S$_2$—O$^-$, $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compounds that can be used as aldoketo reductase (AKR) inhibitors and to their use in modulating protein nitrosylation and treating disorders associated with NO/SNO deficiency. The compounds described herein can have a formula selected from the group consisting of:

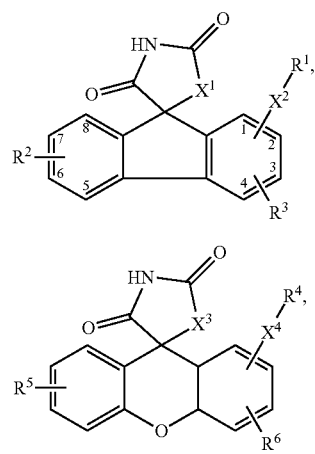

and pharmaceutically acceptable salts thereof;

wherein $X^1$ and $X^3$ are each independently $CH_2$, NH, or O;

$X^2$ and $X^4$ are each independently a linear or branched alkylene, alkylyne, O, or absent;

$R^1$ and $R^4$ are each independently a substituted or unsubstituted cycloalkyl or a substituted or unsubstituted heterocyclyl containing from 4-6 ring atoms (wherein 1 atom of the ring atoms is independently selected from O);

$R^2$, $R^3$, $R^5$, and $R^6$ are each independently H, a halo group, $C_1$-$C_6$ alkyl, $C_1$-$C_6$ alkoxy, $C_1$-$C_6$ alkylsulfide, $C_1$-$C_6$ alkylsulfinyl, $C_1$-$C_6$ alkylsulfonyl, —$CF_3$, —S—$CF_3$, —$SO_2CF_3$, CO—N($R^a$)—$R^6$, $C_1$-$C_6$ alkyl alcohol, $C_1$-$C_6$ alkyl ether, nitro, $C_1$-$C_6$ alkyl sulfide, $C_1$-$C_6$ alkylamine, $C_1$-$C_6$ alkyl esters, carboxylic acids, $C_1$-$C_6$ cycloalkyl, or $C_1$-$C_6$ heterocyclyl; and $R^a$ and $R^b$ are each independently H or a $C_1$-$C_6$ alkyl.

In some embodiments, the 7-C of the compound of formula (I) does not include an $R^2$ group selected from the group consisting of hydrogen, cyclopropyl, fluoro if the 2-C is a cyclopropyl or cyclobutyl group, $X^1$ is NH, and $X^2$ is absent.

In other embodiments, $R^1$ and $R^4$ are each independently a substituted or unsubstituted cyclopropyl, cyclobutyl, bicyclobutyl, or oxacyclobutyl.

In some embodiments, $X^1$ and $X^3$ are NH.

In other embodiments, $X^2$ and $X^4$ are absent.

In other embodiments, $R^2$, $R^3$, $R^5$, and $R^6$ are each independently H, a halo group, or a $C_1$-$C_6$ alkyl.

In still other embodiments, the compound can have the following formula (III):

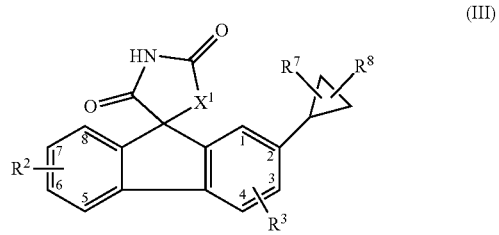

or pharmaceutically acceptable salts thereof;

wherein $X^1$ is $CH_2$, NH, or O;

$R^2$ and $R^3$ are each independently H, a halo group, $C_1$-$C_6$ alkyl, $C_1$-$C_6$ alkoxy, $C_1$-$C_6$ alkylsulfide, $C_1$-$C_6$ alkylsulfinyl, $C_1$-$C_6$ alkylsulfonyl, —$CF_3$, —S—$CF_3$, —$SO_2CF_3$, CO—N($R^a$)—$R^b$, $C_1$-$C_6$ alkyl alcohol, $C_1$-$C_6$ alkyl ether, nitro, $C_1$-$C_6$ alkyl sulfide, $C_1$-$C_6$ alkylamine, $C_1$-$C_6$ alkyl esters, carboxylic acids, $C_1$-$C_6$ cycloalkyl, or $C_1$-$C_6$ heterocyclyl;

$R^a$ and $R^b$ are each independently H or a $C_1$-$C_6$ alkyl; and $R^7$ and $R^8$ are each independently H, a halo group, or $C_1$-$C_6$ alkyl.

In some embodiments, the 7-C of the compound does not include an $R^2$ group selected from the group consisting of hydrogen, cyclopropyl, and fluoro.

In some embodiments, the compound can have a formula selected from the group consisting of:

-continued
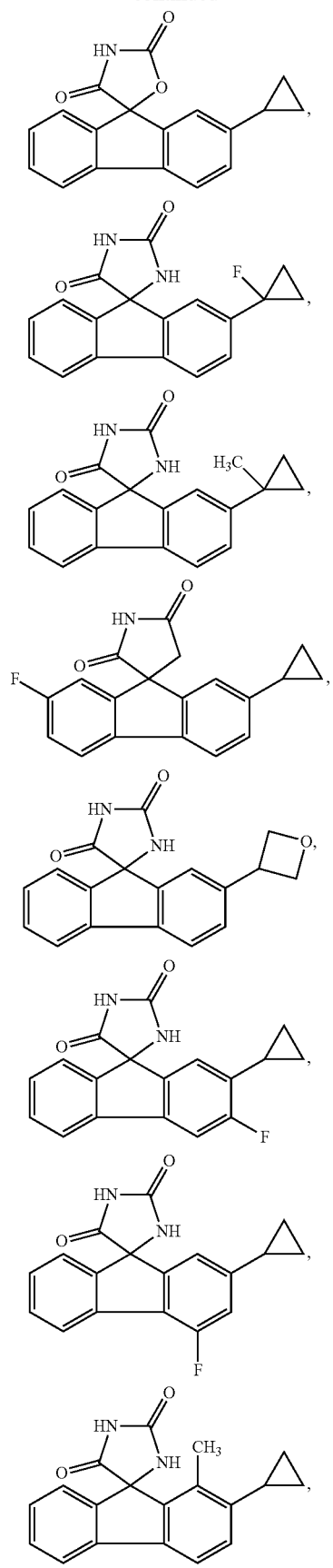
-continued
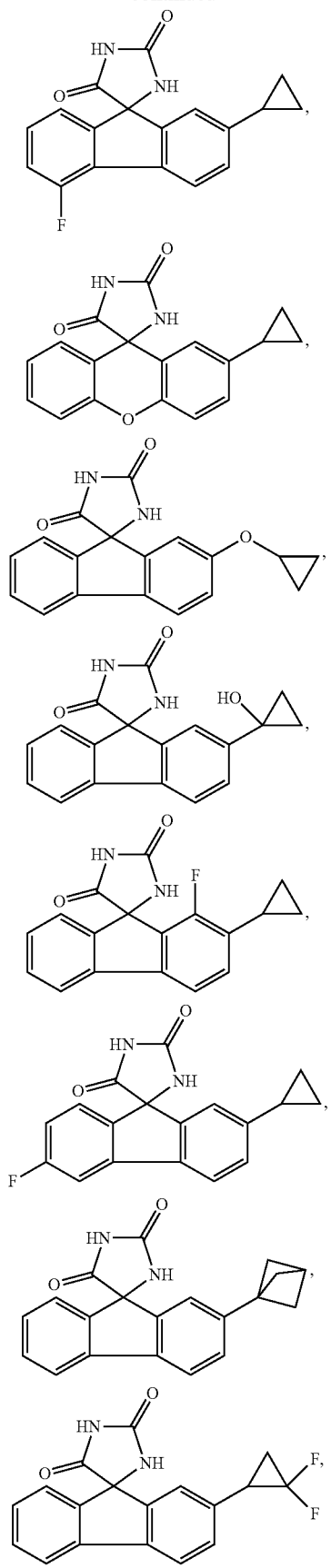

-continued
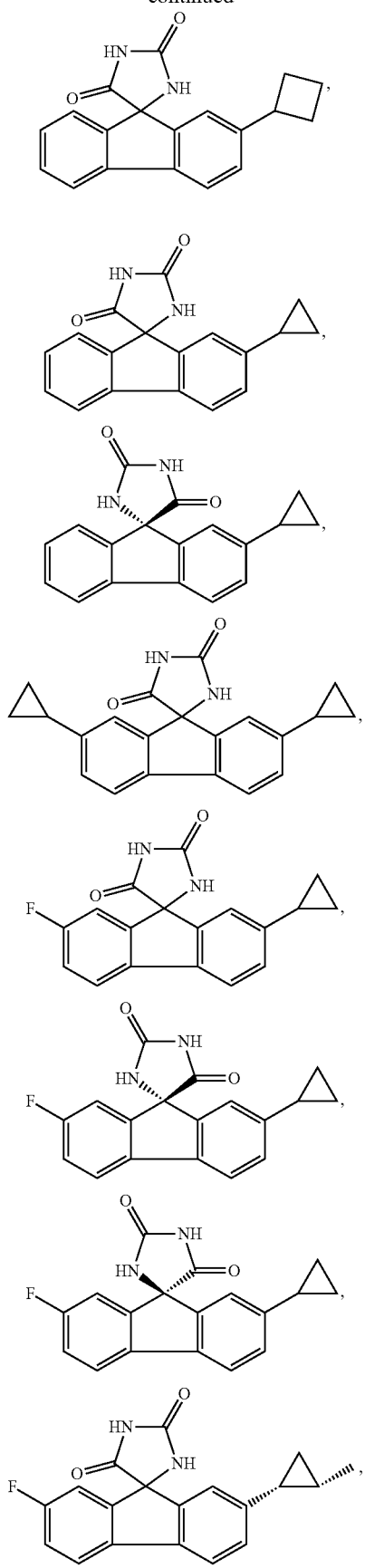
-continued
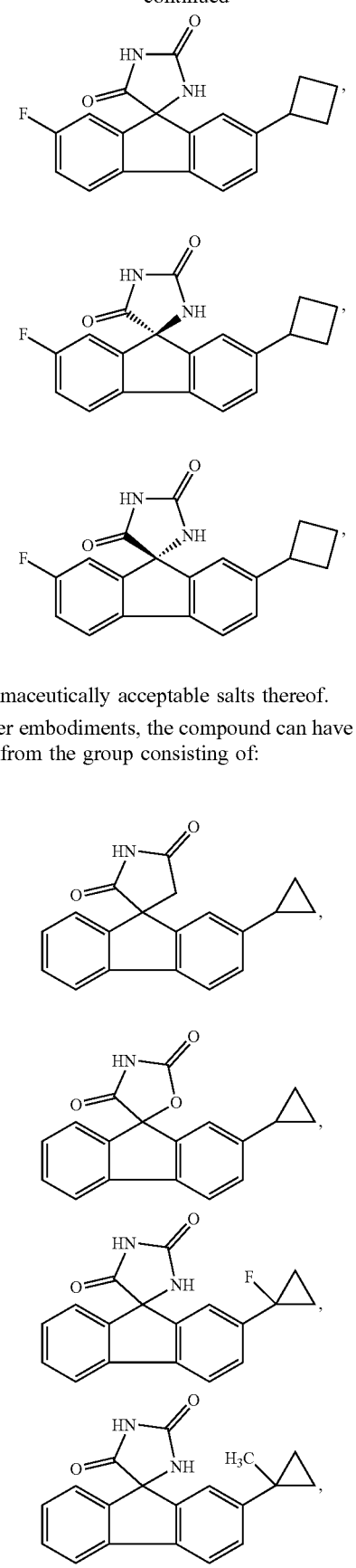
and pharmaceutically acceptable salts thereof.
In other embodiments, the compound can have a formula selected from the group consisting of:

-continued
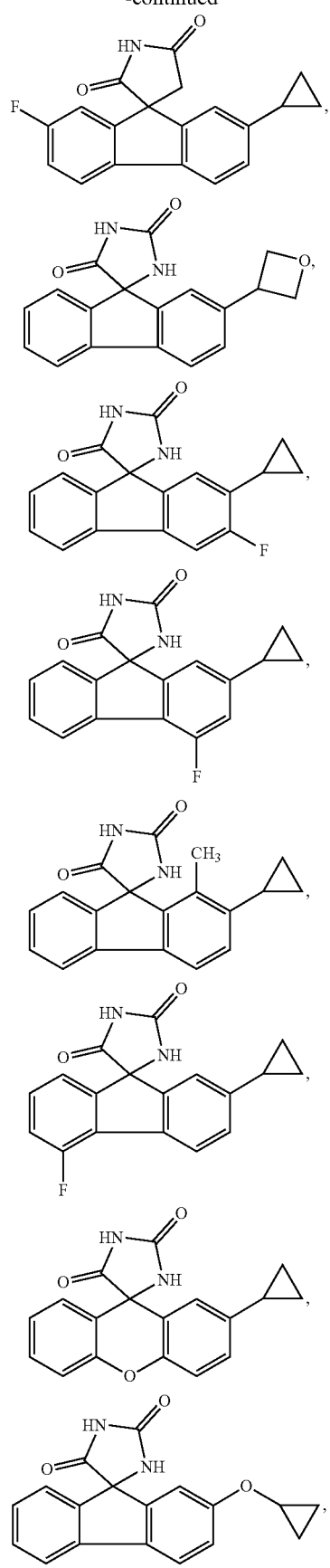
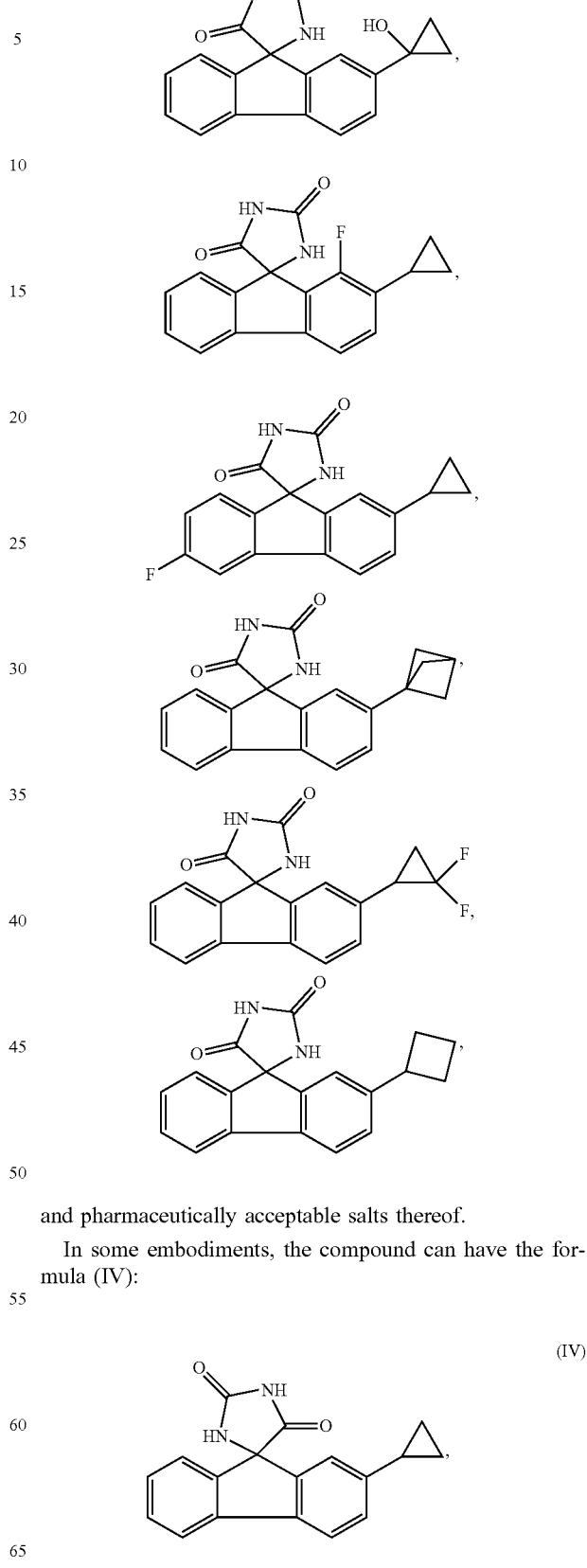
and pharmaceutically acceptable salts thereof.
In some embodiments, the compound can have the formula (IV):
(IV)
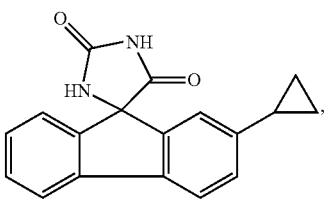
and pharmaceutically acceptable salts thereof.

In other embodiments, the compound can have the following formula (IVa):

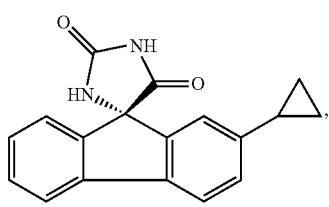

(IVa)

and pharmaceutically acceptable salts thereof.

In other embodiments, the compound can have the following formula (IVb):

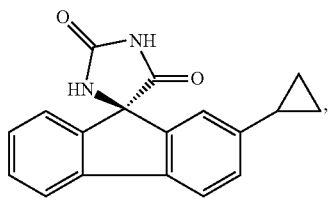

(IVb)

and pharmaceutically acceptable salts thereof.

In other embodiments, the compound can comprise an optical isomer of a compound having formula (IV). In some embodiments, the compound can comprise a mixture of at least one of an IVa or IVb optical isomer of a compound having formula (IV). For example, the compound can comprise a mixture of: less than about 50% by weight of the (IVa) optical isomer and greater than about 50% by weight of (IVb) optical isomer of a compound having formula (IV), less than about 25% by weight of the (IVa) optical isomer of a compound having formula (IV) and greater than about 75% by weight of the (IVb) optical isomer of a compound having formula (IV), less than about 10% by weight of the (IVa) optical isomer of a compound having formula (IV) and greater than about 90% by weight of the (IVb) optical isomer of a compound having formula (IV), less than about 1% by weight of the (IVa) optical isomer of a compound having formula (IV) and greater than about 99% by weight of the (IVb) optical isomer of a compound having formula (IV), greater than about 50% by weight of the (IVa) optical isomer of a compound having formula (IV) and less than about 50% by weight of the (IVb) optical isomer of a compound having formula (IV), greater than about 75% by weight of the (IVa) optical isomer of a compound having formula (IV) and less than about 25% by weight of the (IVb) optical isomer of a compound having formula (IV), greater than about 90% by weight of the (IVa) optical isomer of a compound having formula (IV) and less than about 10% by weight of the (IVb) optical isomer of a compound having formula (IV), or greater than about 99% by weight of the (IVa) optical isomer of a compound having formula (IV) and less than about 1% by weight of the (IVb) optical isomer of a compound having formula (IV).

In a still further embodiment, the compound can consist essentially of or consist of the (IVa) optical isomer of a compound having formula (IV). In yet another embodiment, the compound can consist essentially of or consist of the (IVb) optical isomer of a compound having formula (IV).

In other embodiments, the compound does not have a having a formula selected from the group consisting of:

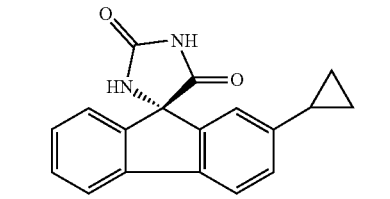

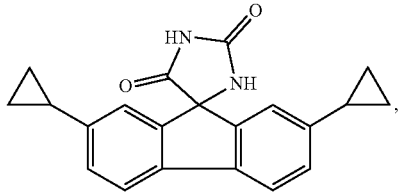

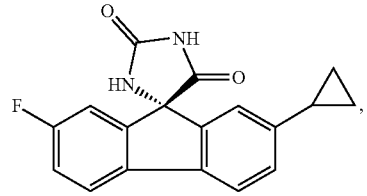

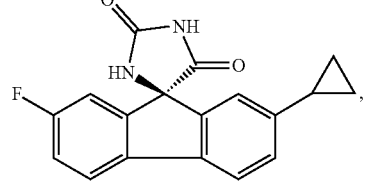

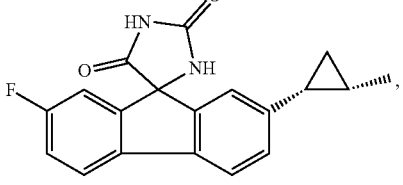

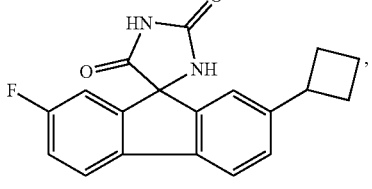

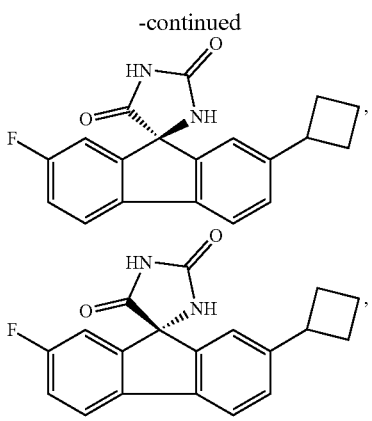

and pharmaceutically acceptable salts thereof.

In some embodiments, the compound can be a partially selective AKR1A1 inhibitor and/or partially selective AKR1B1 inhibitor. For example, the AKR inhibitor can inhibit both AKR1A1 and AKR1B1, inhibit AKR1B1 at a lower $IC_{50}$ than AKR1A1, or inhibit AKR1A1 at a lower $IC_{50}$ than AKR1B1.

In some embodiments, the AKR1A1 inhibitor can have an $IC_{50} \leq 5$ µM, $\leq 1$ µM, or $\leq 100$ nM. In other embodiments, the AKR1A1 inhibitor can have a selectivity for AKR1A1 versus AKR1B1 $\geq 2$ times, $\geq 5$ times, $\geq 10$ times, $\geq 20$ times, $\geq 30$ times, $\geq 40$ times, $\geq 50$ times or more times. In other embodiments, the AKR1A1 inhibitor can have a selectivity for AKR1A1 versus other AKRs $\geq 2$ times, $\geq 5$ times, $\geq 10$ times, $\geq 20$ times, $\geq 30$ times, $\geq 40$ times, $\geq 50$ times or more times. In still other embodiments, the AKR1A1 inhibitor can have an AKR1A1 $IC_{50} \leq 400$ nM, $\leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

In some embodiments, the selectivity of the AKR inhibitor for AKR1A1 inhibition versus other AKRs, such as AKR1B1, can be measured using S-nitroso-Coenzyme A (SNO-CoA) as a substrate. In this instance where SNO-CoA is used as a substrate to measure AKR activity, the AKR inhibitor can have a selectivity for AKR1A1 versus AKR1B1 of $\geq 1$ time, $\geq 2$ times, $\geq 5$ times, $\geq 10$ times, $\geq 20$ times, $\geq 30$ times, $\geq 40$ times, $\geq 50$ times or more. By way of example, JSD-26-1, which is described in the example below, has an AKR1A1/AKR1B1 selectivity of at least 9. In some embodiments, the AKR inhibitor can have negligible inhibition of AKR1B1 activity of SNO-CoA, and particularly compared to AKR1A1 activity.

AKR1A1 was found to reduce SNO-Coenzyme A (SNO-CoA), an endogenous nitrosylating agent, and thus is responsible for denitrosylation of multiple novel proteins. AKR1A1 was also found to metabolize GSNO, a known nitrosylating agent. Inhibition of AKRs (e.g., AKR1A1) can raise SNO levels and increase the S-nitrosylation of unique sets of proteins, which regulate cell metabolism. Administration of AKR inhibitors described herein to a subject can raise SNO levels in the subject, promote protein S-nitrosylation, and treat disorders associated with NO/SNO deficiency.

Multiple diseases and pathological conditions are associated with disruptions in protein S-nitrosylation. For example, it has been shown that storage of red blood cells (RBCs) leads to a rapid depletion of S-nitrosylated hemoglobin (SNO-Hb), a principal regulator of tissue oxygen delivery. In addition, heart disease, diabetes, cystic fibrosis, asthma, sickle cell disease, pulmonary hypertension, stroke, multiple sclerosis, and ischemia are among the many conditions characterized by diminished SNOs. Loss of SNO-Hb also impairs the ability of banked blood to dilate blood vessels after transfusion, resulting in exacerbation rather than correction of anemia-induced reduction in tissue oxygenation. Additionally, SNO CoA-metabolizing enzymes are identified as regulators of cholesterol metabolism and sterol biosynthesis and of cellular metabolism and have regenerative potential.

Accordingly, in some embodiments AKR inhibitors described herein can be administered to a subject to raise SNO levels and increase S-nitrosylation of proteins in the subject and treat disorders associated with NO/SNO deficiency or disruptions in protein S-nitrosylation, promote maintenance (or restoration) of SNO-Hb levels ("renitrosylation"), lower cholesterol levels, treat ischemia, and treat disorders associated with NO/SNO deficiency, such as cystic fibrosis, asthma, inflammatory bowel disease, hypertension, heart failure, acute coronary syndromes, impotence, stroke, septic shock, as well as promote liver regeneration, kidney regeneration, protect against neurodegenerative diseases (e.g., Alzheimers, Parkinson's, ALS, Huntington's, traumatic brain injury, stroke), promoting stem cell enhancement, antimicrobial activity, and protect against ischemic injury, including renal ischemia and cardiac ischemia.

In some embodiments, the AKR inhibitors described herein can be provided in a pharmaceutical composition. The compositions comprising AKR inhibitors can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the AKR inhibitors can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory disorders, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions for injectable use may comprise sterile aqueous solutions (where water soluble) or dispersions and sterile powders for the extemporaneous preparation of sterile injectable solutions or dispersion. For intravenous administration, carriers include physiological saline, bacteriostatic water, Cremophor EL (BASF, Parsippany, N.J.), or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredient. In the case of sterile powders for the preparation of sterile injectable solutions, examples of methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compounds described herein can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, AKR inhibitors described herein can be prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds described herein may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

In some embodiments, pharmaceutical compositions that include the AKR inhibitors can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, silicified microcrystalline cellulose, gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crosspovidone, sodium starch glycolate, and mixtures thereof; (4) lubricants, including agents that act on the flowability of a powder to be compressed, include magnesium stearate, colloidal silicon dioxide, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose; lactose such as lactose monohydrate, and lactose anhydrous; dibasic calcium phosphate, mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In some embodiments, the AKR inhibitors described herein can be used in methods for preventing or treating (e.g., alleviating one or more symptoms of) medical conditions. The methods comprise administering a therapeutically effective amount of the AKR inhibitors to a patient or subject in need thereof. The compositions can also be used for prophylactic therapy.

The patient can be any animal, domestic, livestock, or wild, including, but not limited to cats, dogs, horses, pigs, and cattle, and preferably human patients. As used herein, the terms patient and subject may be used interchangeably.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

In some embodiments, AKR inhibitors including pharmaceutical compositions comprising the AKR inhibitors can be used in a method of treating a subject afflicted with a disorder ameliorated by NO donor therapy. Such a method comprises administering to a subject a therapeutically effective amount of the AKR inhibitors.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD, acute lung injury); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (ischemic or alcoholic or non-alcoholic or fatty liver disease)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and disorders where regeneration is beneficial including, neurodegenerative conditions (Alzheimers, Parkinson's, ALS etc), acute organ injury, and infections caused by bacteria (e.g., tuberculosis, *C. difficile* infections, among others).

In other embodiments, AKR inhibitors can be used to treat a subject that exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia or acute injury in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, acute kidney injury, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, liver injury, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods can be used for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, pharmaceutical compositions described herein can be used to treat an ischemic tissue in which it is desirable to increase the blood flow, oxygen supply, glucose supply, or supply of nutrients to the tissue.

In one embodiment, AKR inhibitors or a pharmaceutically acceptable salt thereof, or a prodrug or metabolite thereof, can be administered in combination with an NO donor, including SNO—CoA, which is shown to have novel activity in regulating sterol biosynthesis and CoA metabolism. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN1 which is molsidomine, furoxamines, N-hydroxy(N-nitrosamine), and perfluorocarbons that have been saturated with NO or a hydrophobic NO donor. The AKR inhibitors described herein can also be combined with an R(+) enantiomer of amlodipine, a known NO releaser (Zhang at al., J. Cardiovasc. Pharm. 39: 208-214 (2002)).

In some embodiments, the AKR inhibitors can be administered in a combinatorial therapy or combination therapy that includes administration of the AKR inhibitors with one or more additional active agents. The phrase "combinatorial therapy" or "combination therapy" embraces the administration of the AKR inhibitors and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the AKR inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5α-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11): 1465-1473).

Other active compounds, which can be present in pharmaceutical and/or cosmetic compositions can include aminexil and its derivatives, 604(9Z,12Z)octadec-9,12-dienoylhexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium pantotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

Still other embodiments described herein relate to a method of treating a subject afflicted with pathologically proliferating cells where the method comprises administering to the subject a therapeutically effective amount of the AKR inhibitors.

In some embodiments, the pathologically proliferating cells can be pathologically proliferating mammalian cells. The term "pathologically proliferating mammalian cells" as used herein means cells of the mammal that grow in size or number in the mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In some embodiments, treating cancer can include a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the AKR inhibitors described herein can be administered in combination with a second chemotherapeutic agent or biologic. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, AKR inhibitors can be administered in combination with an agent that imposes nitrosative or oxidative stress. Agents for selectively imposing nitrosative stress to inhibit proliferation of pathologically proliferating cells in combination therapy with the AKR inhibitors and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with the AKR inhibitors include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

The AKR inhibitors may also be co-administered with a phosphodiesterase inhibitor (e.g., rolipram, cilomilast, roflumilast, VIAGRA (sildenifil citrate), CIALIS (tadalafil), LEVITRA (vardenifil), etc.), a β-agonist, a steroid, or a leukotriene antagonist (LTD-4). Those skilled in the art can readily determine the appropriate therapeutically effective amount depending on the disorder to be ameliorated.

The AKR inhibitors may be used as a means to improve β-adrenergic signaling. In particular, AKR inhibitors alone or in combination with β-agonists could be used to treat or protect against heart failure, or other vascular disorders, such as hypertension and asthma. The AKR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

In some embodiments, a therapeutically effective amount of the AKR inhibitor described herein for the treatment of a subject afflicted with a disorder ameliorated by NO donor therapy is an AKR and/or SNO-CoAR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means an AKR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

The invention is further illustrated by the following examples, which is not intended to limit the scope of the claims.

EXAMPLE

Synthesis of Compound

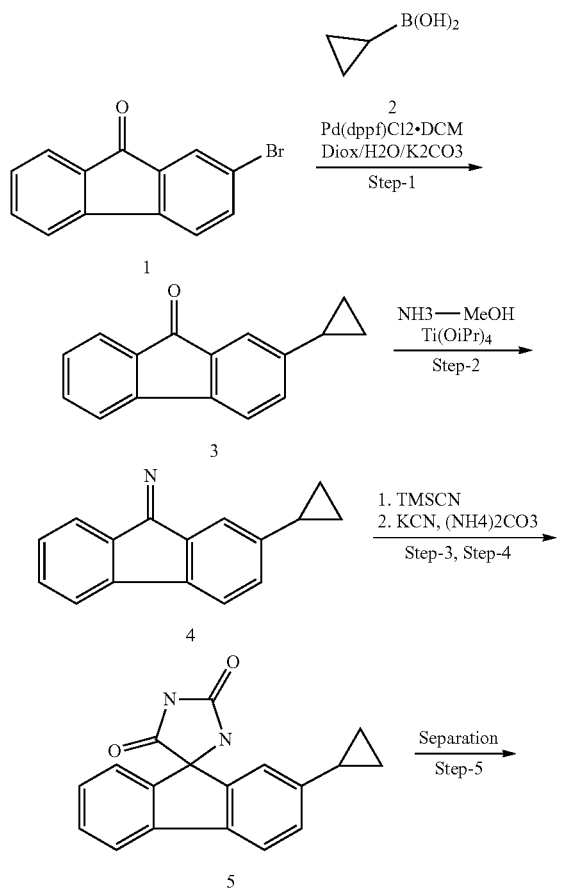

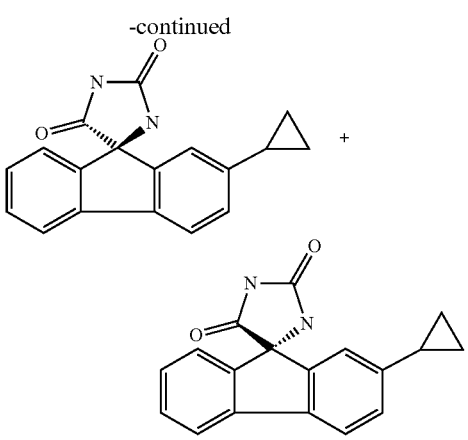

Step-1 (Synthesis of compound 3)

To a stirred solution of compound 1(1 g, 3.86 mmol) and compound 2(0.996 g, 11.53 mmol) in Dioxane: Water (20 mL: 5 mL) was added $K_2CO_3$ (1.6 g, 11.58 mmol) under Na atmosphere. The reaction mixture was degassed with nitrogen over 15 min followed by addition of $Pd(dppf)Cl_2.DCM$ (0.315 g, 0.386 mmol) and again degassed for another 10 min, heated to 80° C. for 16 h. After completion, reaction mixture was filtered through a small pad of Celite, washed with ethyl acetate, water was added, extracted with ethyl acetate, washed with water followed by brine, dried over anhydrous sodium sulphate, filtered, evaporated under reduced pressure to afford the crude mass which was purified by column chromatography (10% EA/HEX) to afford the desired compound 3(800 mg, 94%) as an yellow gum.

Step-2 (Synthesis of Compound 4)

To the stirred solution of compound 3 (1 g, 4.54 mmol) in methanolic ammonia (5 ml), titanium isopropoxide (1.5 ml, 13.63 mmol) was added at 0° C. in a sealed tube and the reaction mixture was then allowed to stir at 60° C. for 12 h. After complete consumption of the starting material (monitored by TLC), it was filtered and forwarded to the next step without workup.

Step-3 and Step-4 (Synthesis of Compound 5)

To the above stirred solution of crude compound 4 (2 g) in methanolic ammonia (10 ml), TMSCN(3.42 ml, 27.27 mmol) was added slowly, purged with nitrogen and stir for 2 h at rt followed by heating at 60 C for 12 hr in sealed tube. The reaction mixture was diluted with ethyl acetate and water and the resulting slurry was filtered through celite pad, filtrate thus collected dried over anhydrous $N_2SO_4$, filtered, concentrated under reduced pressure to afford crude (1.8 g) which was used directly in the next reaction.

Figure 2:
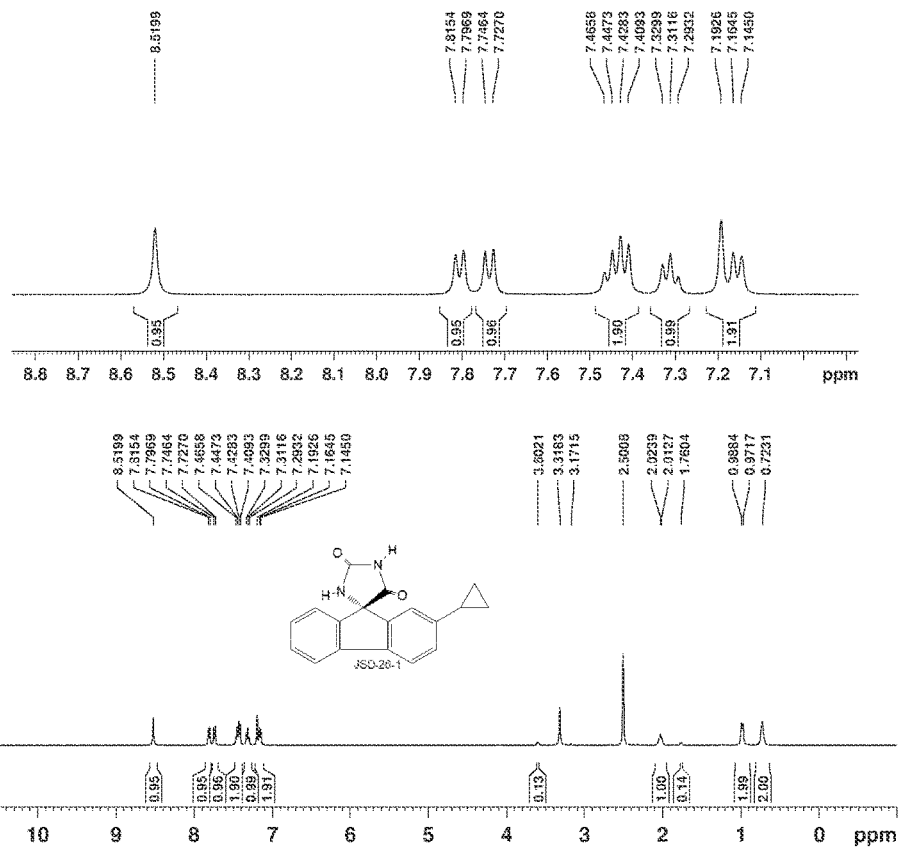
Figure 3:
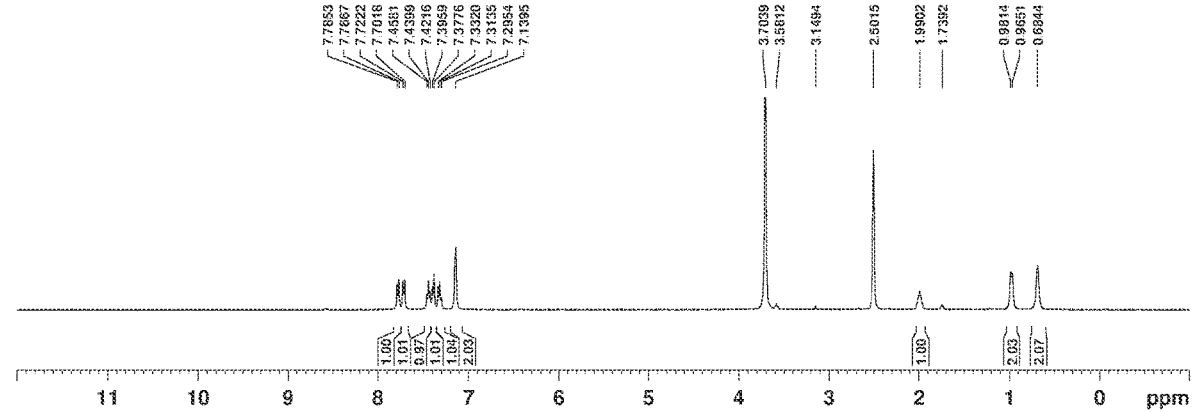
Figure 4:
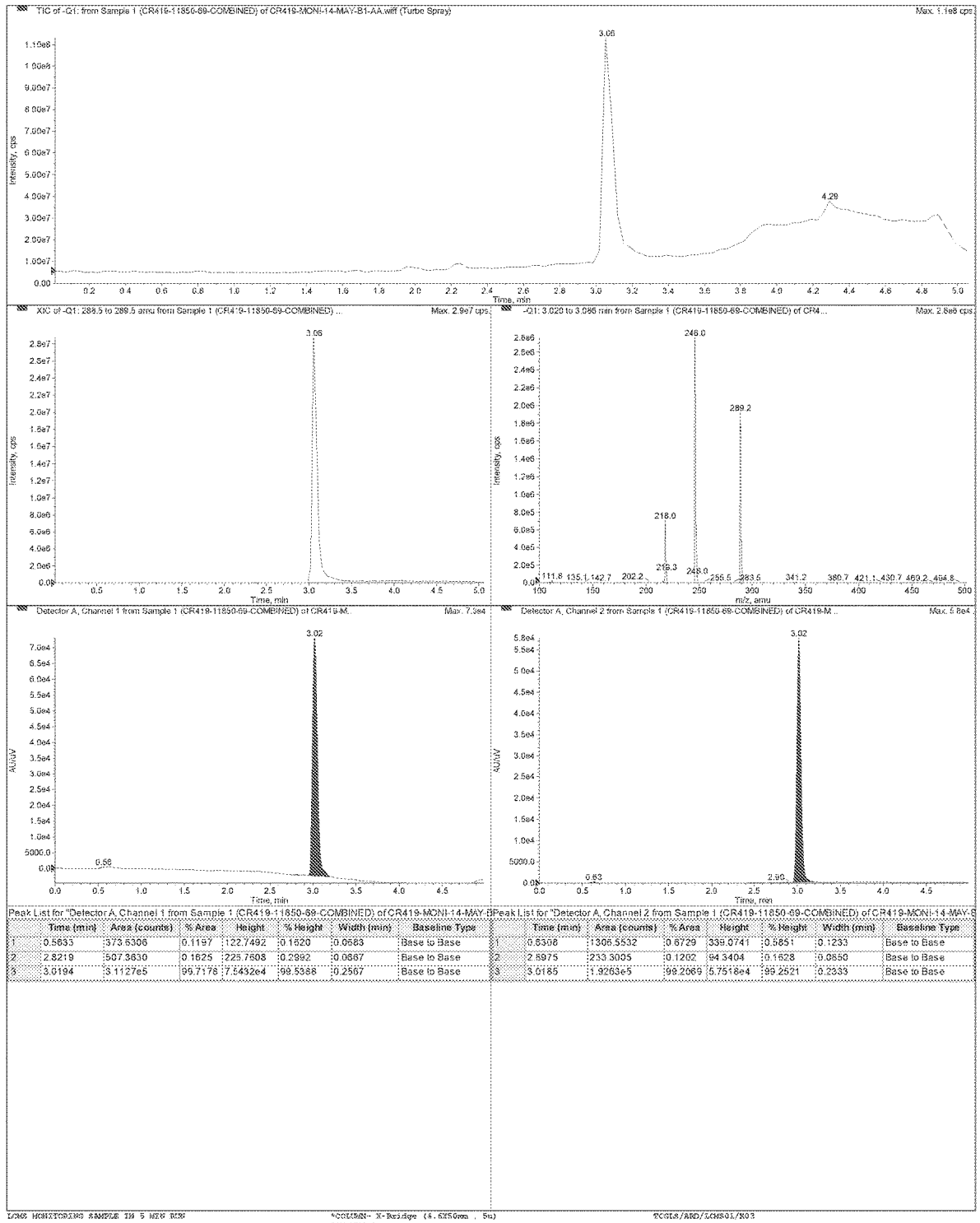

To a stirred solution of the above crude in Methanol was added KCN (1.77 g, 27.27 mmol) and ammonium carbonate (8.73 g, 90.90 mmol) in a sealed tube and heated at 80° C. for 48 h. After complete consumption of the starting material (monitored by TLC), the reaction mass was quenched with 3N HCl till acidic and diluted with water and ethyl acetate. The organic layer was separated and the aqueous layer extracted with ethyl acetate (3×100 ml), washed with water followed by brine, dried over anhydrous sodium sulfate, filtered, evaporated under reduced pressure to afford the crude mass which was purified by column chromatography (30% EA/HEX) to afford the desired compound 6 (400 mg, 20%) as an white solid. As shown in the chromatography and nuclear magnetic resonance results in FIGS. 1-4 the more active enantiomer was shown as peak 1.

Chiral HPLC Method

Chiral HPLC was done by Agilent-HPLC 1200 Series following the mentioned method:

Column—Chiralpak IC (4.6×250 mm), 5μ
Mobile phase—Hexane/EtOH/IPamine: 80/20/0.1
Flow rate—1.0 ml/min
Run time—15 min
Wave length—282 nm
Solubility—Methanol From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A compound having the formula

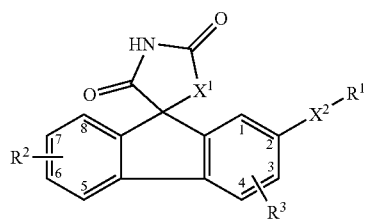

and pharmaceutically acceptable salts thereof;
wherein $X^1$ is $CH_2$, NH, or O;
$X^2$ is O, or absent;
$R^1$ is a substituted or unsubstituted cyclopropyl, cyclobutyl, bicyclobutyl, oxacyclobutyl, or cyclopentyl;
and $R^2$ and $R^3$ are each independently H, a fluoro group, or a $C_1$-$C_6$ alkyl.

2. The compound of claim 1, wherein $X^1$ is NH.

3. The compound of claim 1, wherein $X^2$ is absent.

4. The compound of claim 1, wherein the 7-C of the compound does not include an $R^2$ group selected from the group consisting of hydrogen, cyclopropyl, and fluoro.

5. The compound of claim 1, having a formula selected from the group consisting of:

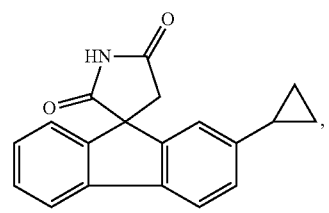

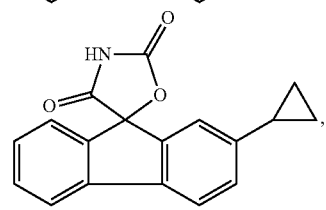

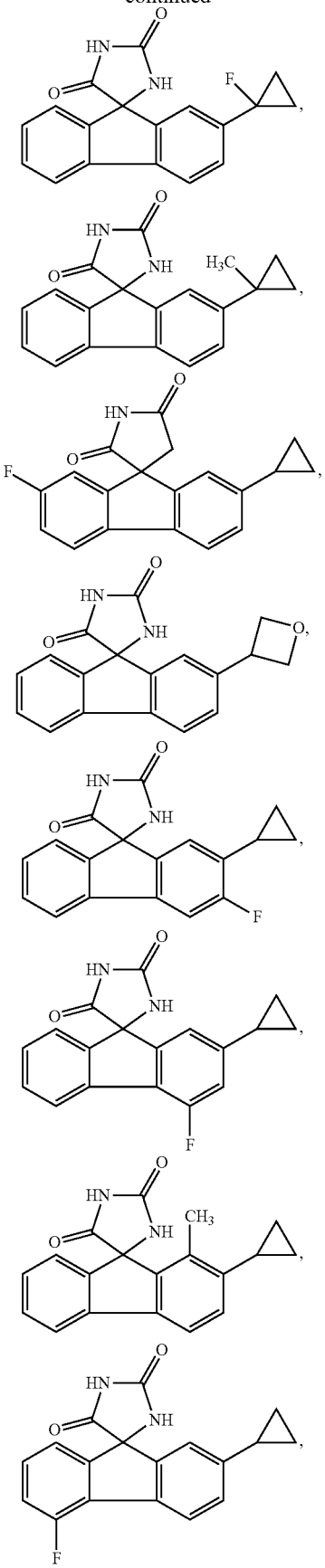

-continued

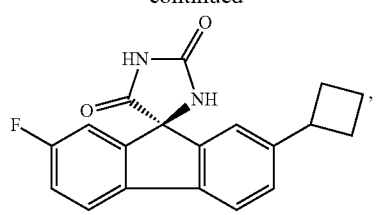
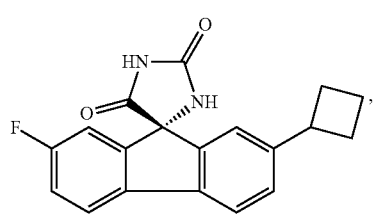 [SMILES: O=C1NC(=O)[C@]2(N1)c1cc(F)ccc1-c1ccc(C3CCC3)cc12]
and pharmaceutically acceptable salts thereof.
6. The compound of claim 1, having a formula selected from the group consisting of:
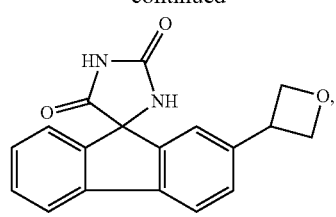
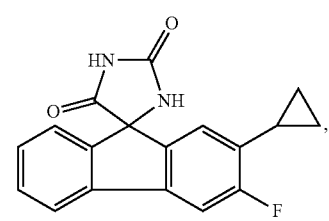
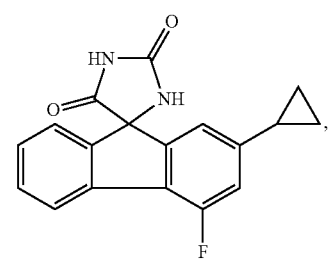
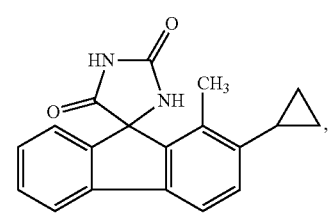
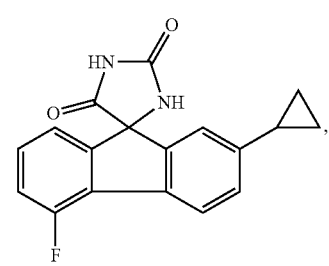
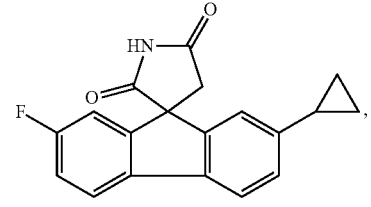
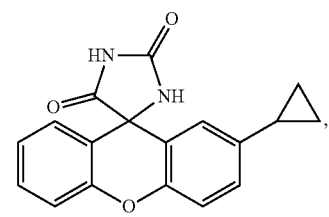
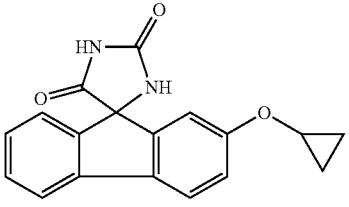
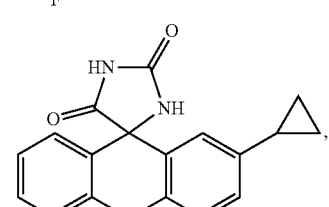
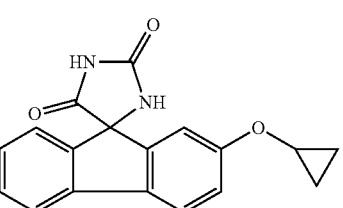
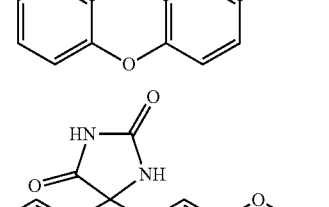
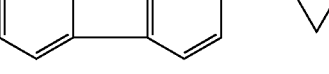

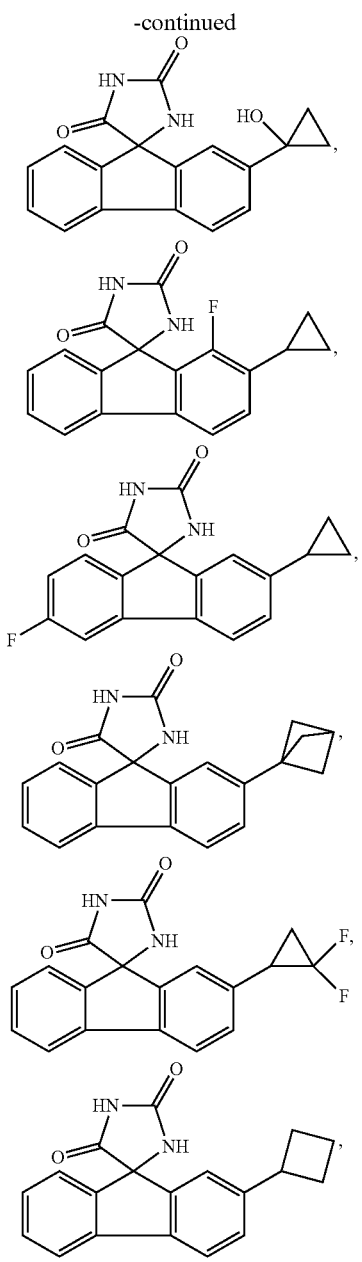

and pharmaceutically acceptable salts thereof.

7. A method of inhibiting an aldoketo reductase (AKR) in a subject, the method comprising;

administering to the subject a compound of claim 1.

8. The method of claim 7, wherein the compound is a selective or partially selective AKR1A1 inhibitor.

9. The method of claim 8, wherein the compound has a AKR1A1 to AKR1B1 selectivity (AKR1A1/AKR1B1) of at least about 6, at least about 7, at least about 8, at least about 9, at least about 10, at least about 11, at least about 12, at least about 13, at least about 14, at least about 15 or more.

10. The method of claim 7, the compound being administered to a subject at an amount effective to increase S-nitrosylation of proteins in the subject.

11. The method of claim 7, the compound being administered to a subject in need thereof to treat disorders associated with NO/SNO deficiency or those benefiting from increased SNO in a subject.

12. The method of claim 7, the compound being administered at an amount effective to increase SNO levels in blood or tissue of a subject in need thereof.

13. The method of claim 11, wherein the disorder comprises ischemia.

14. The method of claim 13, wherein the ischemia comprises ischemic tissue or tissue damaged by ischemia.

15. The method of claim 7, the compound being administered to a subject to treat at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasia, ischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's, alzheimer's disease, or other neurodegenerative disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, liver injury, or wounds to tissues, skin, or organs.

16. The compound of claim 1, the compound having the formula:

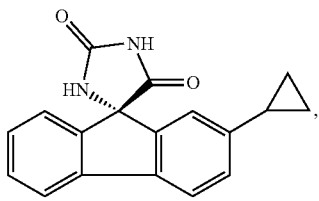 [SMILES: O=C1NC(=O)[C@]2(N1)c1ccccc1-c1ccc(C3CC3)cc12]

and pharmaceutically acceptable salts thereof.

* * * * *